United States Patent [19]

Meier et al.

[11] Patent Number: 5,731,333
[45] Date of Patent: Mar. 24, 1998

[54] 4-PHENYL-3-SUBSTITUTED 1,4-DIHYDROPYRIDINE ESTERS

[75] Inventors: Heinrich Meier, Higashi-Nada-Ku, Japan; Wolfgang Hartwig, Stamford, Conn.; Bodo Junge; Rudolf Schohe-Loop, both of Wuppertal, Germany; Zhan Gao, Beijing, China; Bernard Schmidt, Lindlar, Germany; Maarten de Jonge, Overath, Germany; Teunis Schuurman, Lohmar, Germany

[73] Assignee: Bayer Aktiengesellschaft, Leverkusen, Germany

[21] Appl. No.: 348,696

[22] Filed: Dec. 2, 1994

[30] Foreign Application Priority Data

Dec. 10, 1993 [DE] Germany .............. 43 42 196.2

[51] Int. Cl.⁶ .................. C07D 211/86; A61K 31/455
[52] U.S. Cl. .............................. 514/356; 546/321
[58] Field of Search .................. 546/321; 514/356

[56] References Cited

U.S. PATENT DOCUMENTS

| | | | |
|---|---|---|---|
| 3,764,683 | 10/1973 | Bossert et al. | 546/321 |
| 3,932,646 | 1/1976 | Meyer et al. | 514/356 |
| 4,044,141 | 8/1977 | Bossert et al. | 546/321 |
| 4,264,611 | 4/1981 | Berntsson et al. | 546/321 |
| 4,406,906 | 9/1983 | Meyer et al. | 514/356 |
| 4,510,310 | 4/1985 | Wehinger et al. | 546/321 |
| 4,559,350 | 12/1985 | Wehinger et al. | 546/270 |
| 4,568,681 | 2/1986 | Wehinger et al. | 514/338 |
| 4,622,332 | 11/1986 | Wehinger et al. | 514/356 |
| 4,849,433 | 7/1989 | Wehinger et al. | 514/356 |
| 4,918,076 | 4/1990 | Opitz et al. | 514/277 |
| 4,956,361 | 9/1990 | Traber et al. | 514/217 |
| 4,988,717 | 1/1991 | Wehinger et al. | 514/356 |
| 5,114,946 | 5/1992 | Lawter et al. | 514/279 |
| 5,137,889 | 8/1992 | Tamada et al. | 544/360 |
| 5,234,935 | 8/1993 | Behner et al. | 546/321 |
| 5,328,931 | 7/1994 | Rosen et al. | 514/356 |
| 5,403,849 | 4/1995 | Schohe-Loop et al. | 514/340 |

FOREIGN PATENT DOCUMENTS

| | | |
|---|---|---|
| 151485 | 10/1970 | Australia . |
| 0007293 | 1/1980 | European Pat. Off. . |
| 0012180 | 6/1980 | European Pat. Off. . |
| 0088940 | 9/1983 | European Pat. Off. . |
| 0525568 | 2/1993 | European Pat. Off. . |
| 0534520 | 3/1993 | European Pat. Off. . |
| 0595164 | 5/1995 | European Pat. Off. . |
| 2218644 | 10/1973 | Germany . |
| 2508181 | 9/1976 | Germany . |
| WO 88/09331 | 12/1988 | WIPO . |

OTHER PUBLICATIONS

Aldrichimica Acta, vol. 18, p. 25 (1985).
Still et al. J. Org. Chem. vol. 43, No. 14, 2923, (1978).
Rampe D.R., Mutledge A., Janis R.A., Triggle D.J.: Can. Journ. Physiol. Pharmacol. vol. 65, 1452, (1987).
CA 103: 123371, 1985.
Journal of Cardiovascular Pharmacology, vol. 10, pp. 560–565 (1986).

*Primary Examiner*—Jane Fan
*Attorney, Agent, or Firm*—Sprung Kramer Schaefer & Briscoe

[57] ABSTRACT

4-Phenyl-3-substituted 1,4-dihydropyridine esters are prepared by reaction of benzaldehydes with ketoesters and enamines, if appropriate with isolation of the ylidene intermediate products, or by esterification of corresponding dihydropyridinecarboxylic acids with alcohols.

The new 4-phenyl-3-substituted 1,4-dihydropyridine esters can be employed as active compounds in medicaments for the treatment of the central nervous system, in particular as cerebral therapeutics.

3 Claims, No Drawings

4-PHENYL-3-SUBSTITUTED 1,4-DIHYDROPYRIDINE ESTERS

The invention relates to 4-phenyl-3-substituted 1,4-dihydropyridine esters, processes for their preparation and their use in medicaments, in particular as agents having a cerebral action.

It is known that some dihydropyridines, such as, for example, nimodipine, have a cerebral activity [cf. German Offenlegungsschrift 28 15 578]. Furthermore, dihydropyridines which carry a halogenophenyl ring in the 4-position are also known (cf. German Offenlegungsschrift 1 963 188, German Offenlegungsschrift 2 117 572, German Offenlegungsschrift 2 117 573 and EP 007 293).

The present invention relates to selected new 4-phenyl-3-substituted 1,4-dihydropyridine esters of the general formula (I)

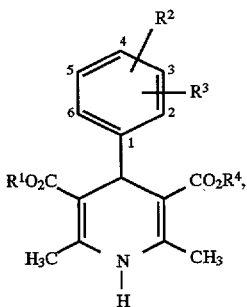

in which
- $R^1$ represents straight-chain or branched alkyl having up to 8 carbon atoms, which is optionally substituted by cycloalkyl having 3 to 6 carbon atoms or by hydroxyl or by straight-chain or branched alkoxy having up to 6 carbon atoms, or represents cycloalkyl having 3 to 8 carbon atoms,
- $R^2$ and $R^3$ are identical or different and represent halogen or cyano, or
- $R^2$ or $R^3$ represents hydrogen,
- $R^4$ represents straight-chain or branched alkyl having up to 8 carbon atoms, which is substituted by cycloalkyl having 3 to 6 carbon atoms, fluorine, cyano, phenyl, pyridine or by a radical of the formula

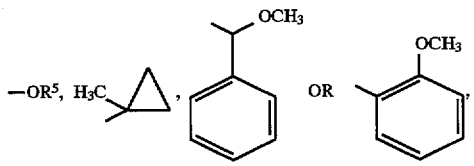

wherein
$R^5$ denotes cycloalkyl having 3 to 6 carbon atoms, straight-chain or branched fluoroalkyl having up to 5 fluorine atoms or straight-chain or branched alkyl having up to 8 carbon atoms, which in turn is substituted by methoxy, ethoxy or cycloalkyl having 3 to 7 carbon atoms, and salts thereof.

Physiologically acceptable salts are salts of the compounds according to the invention with inorganic or organic acids. Preferred salts are those with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid, benzoic acid or methanesulphonic acid, ethanesulphonic acid, phenylsulphonic acid, toluenesulphonic acid or naphthalenedisulphonic acid.

The compounds according to the invention exist in stereoisomeric forms which either behave as mirror images (enantiomers) or do not behave as mirror images (diastereomers). The invention relates both to the antipodes and to the racemic forms, as well as to diastereomer mixtures. The racemic forms, like the diastereomers, can be separated into the stereoisomerically uniform constituents in a known manner.

Preferred compounds of the general formula (I) are those in which
- $R^1$ represents straight-chain or branched alkyl having up to 6 carbon atoms, which is optionally substituted by cyclopropyl, cyclopentyl, cyclohexyl, hydroxyl or by straight-chain or branched alkoxy having up to 5 carbon atoms, or represents cyclopentyl, cyclohexyl or cycloheptyl,
- $R^2$ and $R^3$ are identical or different and represent fluorine, chlorine, bromine or cyano, or
- $R^2$ or $R^3$ represents hydrogen,
- $R^4$ represents straight-chain or branched alkyl having up to 6 carbon atoms, which is substituted by fluorine, cyano, phenyl, pyridine, cyclopropyl, cyclopentyl, cyclohexyl or by a radical of the formula

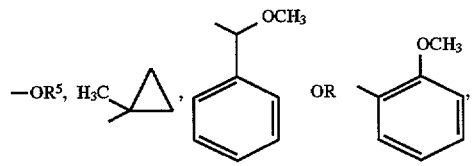

wherein
$R^5$ denotes cyclopropyl, cyclopentyl, cyclohexyl, straight-chain or branched fluoroalkyl having up to 4 fluorine atoms or straight-chain or branched alkyl having up to 6 carbon atoms, which in turn is substituted by methoxy, ethoxy or cyclopropyl,
and salts thereof.

Particularly preferred compounds of the general formula (I) are those
in which
- $R^1$ represents straight-chain or branched alkyl having up to 5 carbon atoms, which is optionally substituted by cyclopentyl, cyclohexyl or by hydroxyl or straight-chain or branched alkoxy having up to 4 carbon atoms, or represents cyclopentyl, cyclohexyl or cycloheptyl,
- $R^2$ and $R^3$ are identical or different and represent fluorine, chlorine, bromine or cyano, or
- either $R^2$ or $R^3$ represents hydrogen,
- $R^4$ represents straight-chain or branched alkyl having up to 5 carbon atoms, which is substituted by fluorine, cyano, cyclopropyl, cyclopentyl, cyclohexyl, phenyl, pyridine or by a radical of the formula

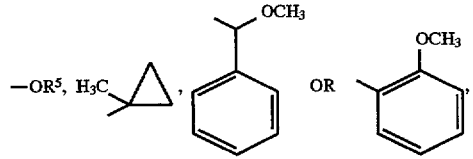

wherein $R^5$ denotes cyclopropyl, cyclopentyl, cyclohexyl, straight-chain or branched fluoroalkyl having up to 3 fluorine atoms or straight-chain or branched alkyl having up to 5 carbon atoms, which in turn is substituted by methoxy or cyclopropyl.

New compounds according to formula (I) are those from the group consisting of 2-cyanoethyl cyclopentyl 4-(2-chloro-6-fluorophenyl)-1,4-dihydro-2,6-dimethylpyridine-3,5-dicarboxylate, cyclopentyl 2-fluoroethyl 4-(2-chloro-6-fluorophenyl)-1,4-dihydro-2,6-dimethylpyridine-3,5-dicarboxylate, cyclohexylmethyl 2-methoxyethyl 4-(3,4-difluorophenyl)-1,4-dihydro-2,6-dimethylpyridine-3,5-dicarboxylate, 2-cyclohexylethyl 2-methoxyethyl 4-(3,4-difluorophenyl)-1,4-dihydro-2,6-dimethylpyridine-3,5-dicarboxylate, 3-cyclohexylpropyl 2-methoxyethyl 4-(3,4-difluorophenyl)-1,4-dihydro-2,6-dimethylpyridine-3,5-dicarboxylate, isopropyl 2-(2-methoxyethoxy) ethyl 4-(2-chloro-6-fluorophenyl) -1,4-dihydro-2,6-dimethylpyridine-3,5-dicarboxylate, cyclopentyl 2-(2-methoxyethoxy) ethyl 4-(2-chloro-6-fluorophenyl) -1,4-dihydro-2,6-dimethylpyridine-3,5-dicarboxylate, isopropyl 2-(2,2,2-trifluoroethoxy)-ethyl 4-(3-cyanophenyl) -1,4-dihydro-2,6-dimethylpyridine-3,5-dicarboxylate, 2-cyclohexyloxyethyl isopropyl 4-(3-cyanophenyl) -1,4-dihydro-2,6-dimethylpyridine-3,5-dicarboxylate, t-butyl 2-(2,2,2-trifluoroethoxy)-ethyl 4-(3-cyanophenyl) -1,4-dihydro-2,6-dimethylpyridine-3,5-dicarboxylate, cyclopentyl 2-(2,2,2-trifluoroethoxy)-ethyl 4-(3-cyanophenyl) -1,4-dihydro-2,6-dimethylpyridine-3,5-dicarboxylate, 2-cyclohexyloxyethyl cyclopentyl 4-(3-cyanophenyl) -1,4-dihydro-2,6-dimethylpyridine-3,5-dicarboxylate, cyclohexylmethyl 2-methoxyethyl 4-(3-cyanophenyl) -1,4-dihydro-2,6-dimethylpyridine-3,5-dicarboxylate, isopropyl-3-phenylpropyl 4-(2,3-dichlorophenyl) -1,4-dihydro-2,6-dimethylpyridine-3,5-dicarboxylate, 2-methoxyethyl 3-phenylpropyl 4-(2,3-dichlorophenyl)-1,4-dihydro-2,6-dimethylpyridine-3,5-dicarboxylate, cyclopropylmethyl 2-methoxyethyl 4-(3-chloro-2-cyanophenyl) -1,4-dihydro-2,6-dimethylpyridine-3,5-dicarboxylate, 2-methoxyethyl (1-methylcyclopropyl)methyl 4-(3-chloro-2-cyanophenyl) -1,4-dihydro-2,6-dimethylpyridine-3,5-dicarboxylate, cyclopentyl 2-(2-pyridyl) ethyl 4-(2,3-difluorophenyl) -1,4-dihydro-2,6-dimethylpyridine-3,5-dicarboxylate, cyclopentyl 2-(2-pyridyl)methyl 4-(2,3-difluorophenyl) -1,4-dihydro-2,6-dimethylpyridine-3,5-dicarboxylate, isopropyl 2-methoxybenzyl 4-(2,3-difluorophenyl) -1,4-dihydro-2,6-dimethylpyridine-3,5-dicarboxylate, isopropyl (S) -methoxy-2-phenylethyl 4- (2,3-difluorophenyl) -1,4-dihydro-2,6-dimethylpyridine-3,5-dicarboxylate, 2-fluoroethyl isopropyl 4-(2,5-difluorophenyl) -1,4-dihydro-2,6-dimethylpyridine-3,5-dicarboxylate, cyclopentyl 2-fluoroethyl 4- (2,5-difluorophenyl)-1,4-dihydro-2,6-dimethylpyridine-3,5-dicarboxylate, isopropyl 2-(2-pyridyl) ethyl 4- (2,3-difluorophenyl) -1,4-dihydro-2,6-dimethylpyridine-3,5-discarboxylate, isopropyl 2- (2-pyridyl)methyl 4-(2,3-difluorophenyl)-1,4-dihydro-2,6-dimethylpyridine-3,5-discarboxylate, 2-cyanoethyl isopropyl 4-(2-chloro-3-cyanophenyl) -1,4-dihydro-2,6-dimethylpyridine-3,5-dicarboxylate, cyclopentyl 2-methoxybenzyl 4-(2,3-difluorophenyl) -1,4-dihydro-2,6-dimethylpyridine-3,5-dicarboxylate, cyclopropyl (S) -2-methoxy-2-phenylethyl 4-(2,3-difluorophenyl) -1,4-dihydro-2,6-dimethylpyridine-3,5-dicarboxylate, isopropyl (R) -2-methoxy-2-phenylethyl 4-(2,3-difluorophenyl) -1,4-dihydro-2,6-dimethylpyridine-3,5-dicarboxylate, methyl 2-(2-pyridyl)ethyl 4-(2,3-difluorophenyl)-1,4-dihydro-2,6-dimethylpyridine-3,5-dicarboxylate, cyclopentylmethyl 2-methoxyethyl 4-(2,3-difluorophenyl)-1,4-dihydro-2,6-dimethylpyridine-3,5-dicarboxylate, cyclopentylmethyl 2-methoxypropyl 4-(2,3-difluorophenyl) -1,4-dihydro-2,6-dimethylpyridine-3,5-dicarboxylate, cyclohexylmethyl 2-methoxyethyl 4-(2,3-difluorophenyl)-1,4-dihydro-2,6-dimethylpyridine-3,5-dicarboxylate, cyclohexylmethyl 2-methoxypropyl 4-(2,3-difluorophenyl)-1,4-dihydro-2,6-dimethylpyridine-3,5-dicarboxylate, cyclohexylmethyl 2-(2-pyridyl)ethyl 4-(2,3-difluorophenyl) -1,4-dihydro-2,6-dimethylpyridine-3,5-dicarboxylate, cyclopentylmethyl 2-(2-pyridyl)ethyl 4-(2,3-difluorophenyl) -1,4-dihydro-2,6-dimethylpyridine-3,5-dicarboxylate, isopropyl 2-(2-pyridyl)ethyl 4-(2-chlorophenyl)-1,4-dihydro-2,6-dimethylpyridine-3,5-dicarboxylate.

Processes have furthermore been found for the preparation of the compounds of the general formula (I) according to the invention, characterized in that

[A] aldehydes of the general formula (II)

in which $R^2$ and $R^3$ have the meanings given, are first reacted with acetoacetic acid esters of the general formula (III)

in which $R^1$ has the meaning given, if appropriate with isolation of the corresponding ylidene compounds of the general formula (IV)

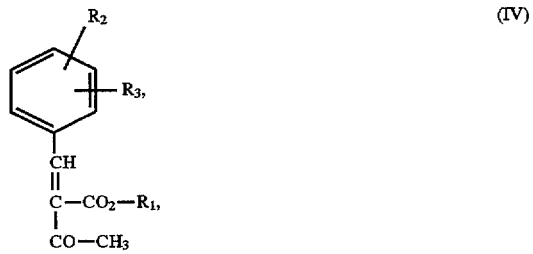

in which $R^1$, $R^2$ and $R^3$ have the meanings given, and the products are then either reacted with compounds of the general formula (V)

in which $R^4$ has the meaning given, in inert solvents in the presence of ammonia or ammonium salts, or are reacted directly with enamino derivatives of the general formula (VI)

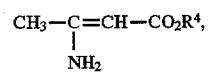  (VI)

in which

R⁴ has the meaning given, or

[B] the aldehydes of the general formula (II) are first reacted with the compounds of the general formula (V), if appropriate with isolation of the ylidene compounds of the general formula (VII)

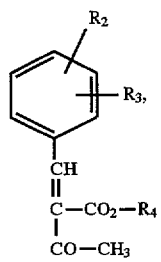  (VII)

in which $R^2$, $R^3$ and $R^4$ have the meanings given, and in a next step the products are reacted with the compounds of the general formula (III) in inert solvents in the presence of ammonia or ammonium salts, or are reacted directly with enaminocarboxylic acid derivatives of the general formula (VIII)

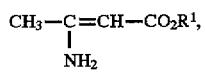  (VIII)

in which $R^1$ has the meaning given, or

[C] compounds of the general formula (IX)

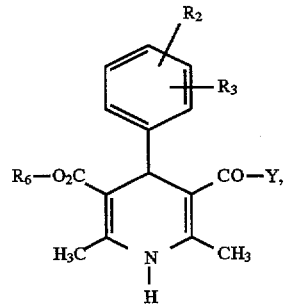  (IX)

in which $R^2$ and $R^3$ have the meanings given, $R^6$ comprises the scope of meanings given for $R^1$ or $R^4$, and Y together with the —CO group forms a reactive carboxylic acid derivative, are reacted in inert solvents in the presence of a base with compounds of the general formula (X)

R⁷—OH  (X)

in which $R^7$ has the meaning given for $R^6$, and, in the case of the pure ester enantiomers, the enantiomerically pure carboxylic acids are reacted with the corresponding alcohols, if appropriate initially via the stage of a reactive acid derivative.

The process according to the invention can be illustrated by way of example by the following equation:

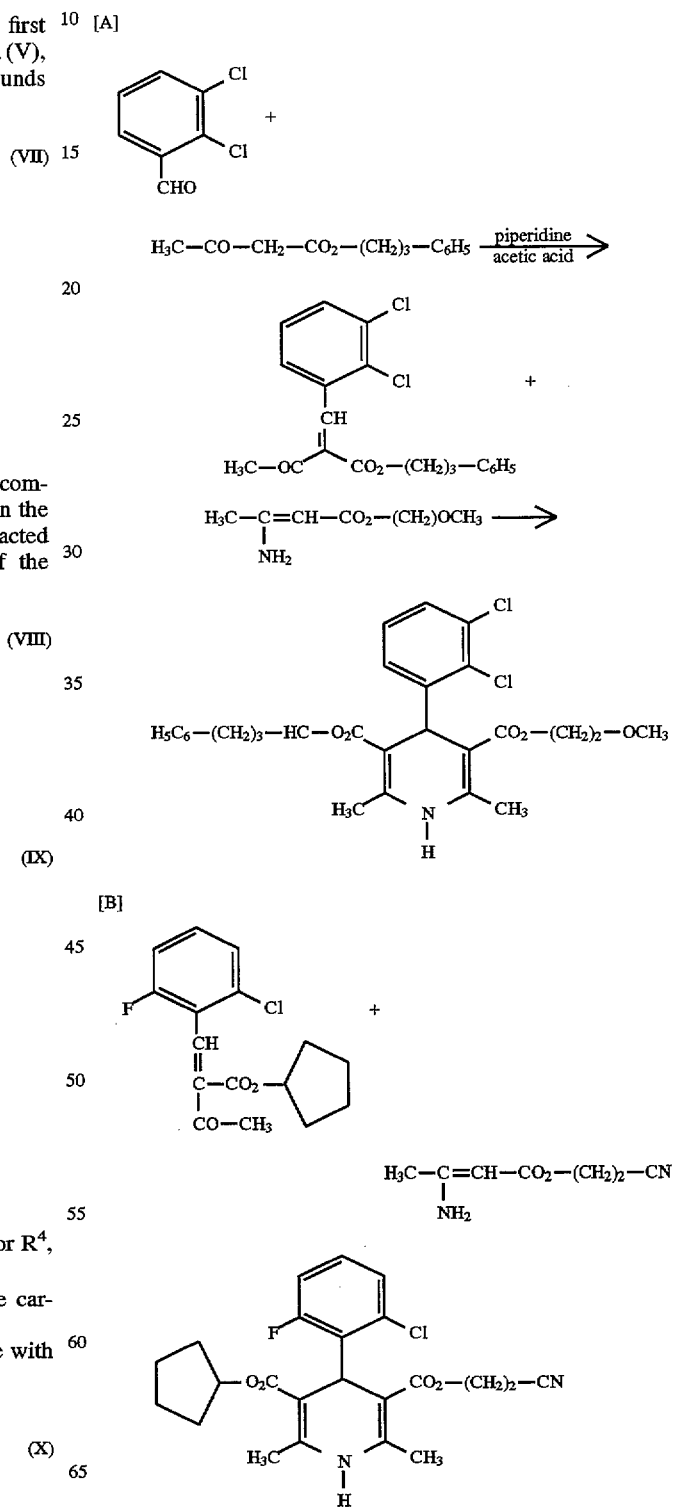

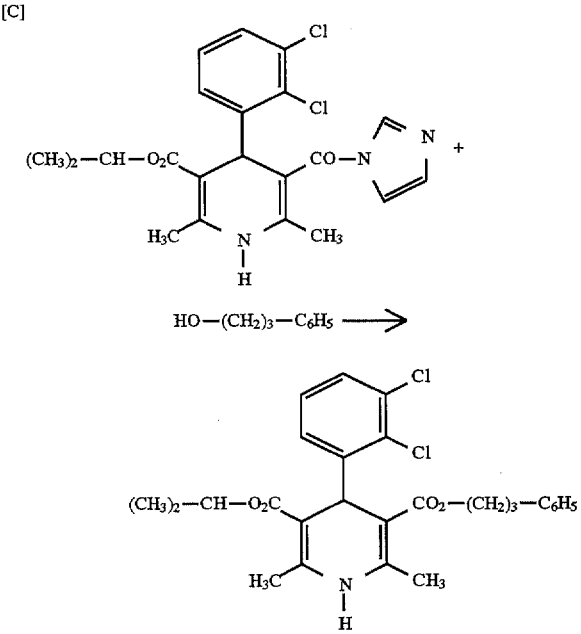

Suitable solvents here for processes [A] and [B] are all the inert organic solvents which do not change under the reaction conditions. These include, preferably, alcohols, such as methanol, ethanol, propanol or isopropanol, or ethers, such as diethyl ether, dioxane, tetrahydrofuran, glycol dimethyl ether or diethylene glycol dimethyl ether, acetonitrile, or amides, such as hexamethylphosphoric acid triamide or dimethylformamide, or acetic acid or halogenated hydrocarbons, such as methylene chloride or carbon tetrachloride, or hydrocarbons, such as benzene or toluene. It is also possible to use mixtures of the solvents mentioned. Isopropanol, tetrahydrofuran, methanol, dioxane and dimethylformamide are preferred.

Suitable solvents for process [C] are the abovementioned solvents, with the exception of the alcohols and acetic acid.

Suitable bases for activation of the carboxylic acids are in general alkali metal hydrides or alcoholares, such as, for example, sodium hydride or potassium tert-butylate, or cyclic amines, such as, for example, piperidine, dimethylaminopyridine or $C_1$–$C_4$-alkylamines, such as, for example, triethylamine. Piperidine, dimethylaminopyridine, pyridine, sodium hydride and potassium tert-butylate are preferred, depending on the particular reaction steps.

Auxiliaries which are preferably employed are condensation agents, which can also be bases. The customary condensation agents are preferred here, such as carbodiimides, for example N,N'-diethyl-, N,N '-dipropyl-, N,N'-diisopropyl- or N,N'-dicyclohexylcarbodiimide or N-(3-dimethylaminoisopropyl) -N'-ethylcarbodiimide hydrochloride, or carbonyl compounds, such as carbonyldiimidazole, or 1,2-oxazolium compounds, such as 2-ethyl-5-phenyl 1,2-oxazolium 3-sulphonate or 2-tert-butyl-5methylisoxazolium perchlorate, or acylamino compounds, such as 2-ethoxy-1-ethoxycarbonyl-1,2-dihydroquinoline, or propanephosphonic acid anhydride, or isobutyl chloroformate, or benzotriazolyloxy-tris (dimethylamino)phosphonium hexafluorophosphonate. N,N'-Dicyclohexylcarbodiimide and carbonyldiimidazole are preferred.

Suitable bases are in general alkali metal carbonates, such as, for example, sodium carbonate or potassium carbonate, or organic bases, such as trialkylamines, for example triethylamine, N-ethylmorpholine, N-methylpiperidine or diisopropylethylamine, or dimethylaminopyridine, 1,8-diazabicyclo[5.4.0]undec-7-ene (DBU) or 1,5-diazabicyclo [4.3.0]non-5-ene (DBN). Dimethylaminopyridine is preferred.

The base is in general employed in an amount of from 0.01 mol to 1 mol, preferably from 0.05 mol to 0.1 mol, in each case per mol of compounds of the general formulae (II) or (IX).

The auxiliaries are in general employed in an amount of from 1 mol to 3 mol, preferably from 1 mol to 1.5 mol, in each case per mol of compounds of the general formulae (II) and (IX).

The reaction temperatures for processes [A] and [B] can be varied within a relatively wide range. In general, the reactions are carried out in a range from—20° C. to 200° C., preferably from 0° C. to 100° C.

The processes can be carried out under normal pressure or increased or reduced pressure (for example from 0.5 to 5 bar), preferably under normal pressure.

Any desired ratio of the substances participating in the reaction can be used for carrying out the processes according to the invention. In general, however, the process is carried out with molar amounts of the reactants.

The customary reagents are suitable for activation of the carboxylic acid, such as inorganic halides, for example thionyl Chloride, phosphorus trichloride or phosphorus pentachloride, or carbonyldiimidazole, carbodiimides, such as cyclohexylcarbodiimide or 1-cyclohexyl-3-[2-(N-methylmorpholino) ethyl]-carbodiimide p-toluenesulphonate, or N-hydroxyphthalimide or N-hydroxy-benzotriazole.

Enantiomerically pure forms are furthermore obtained, for example, by separating diastereomer mixtures of the compounds of the general formula (I), in which $R^1$ or $R^4$ is derived from an enantiomerically pure chiral alcohol, by a customary method, subsequently preparing the enantiomerically pure carboxylic acids and then, if appropriate, converting these into the enantiomerically pure dihydropyridines by esterification with corresponding alcohols.

Suitable chiral ester radicals are all the esters of enantiomerically pure alcohols, such as, for example, 1-phenylethanol, lactic acid, lactic acid esters, mandelic acid, mandelic acid esters, 2-amino-alcohols, sugar derivatives and many other enantiomerically pure alcohols.

The separation of the diastereomers is in general carried out either by fractional crystallization, by column chromatography or by Craig partition. The optimum process must be decided upon from case to case, and sometimes it is also expedient to use combinations of the individual processes.

The enantiomerically pure dihydropyridines are preferably esterified in ethers, such as diethyl ether or tetrahydrofuran, dimethylformamide, methylene chloride, chloroform, acetonitrile or toluene.

The aldehydes of the general formula (II) are known per se or can be prepared by customary methods.

The acetoacetic acid esters of the general formulae (III) and (V) and the enamino derivatives of the general formulae (VI) and (VIII) likewise are known.

The reactive acid derivatives of the general formula (IX) are known in some cases or are new, and can then be prepared by customary methods.

The compounds of the general formula (X) are known per se.

The compounds of the general formula (IV) and (VII) are known in most cases or can be prepared by customary methods.

The above preparation processes are given merely for illustration. The preparation of the compounds of the general formula (I) is not limited to these processes, but any modification of these processes can be used in the same manner for the preparation of the compounds according to the invention.

The compounds according to the invention display an unforeseeable, useful pharmacological action spectrum.

The compounds according to the invention are calcium channel ligands having a selectivity for L-type calcium channels of the central nervous system. This selectivity can be demonstrated, for example, by comparison of the binding affinities to DHP binding sites in the rat brain and rat heart.

The compounds positively influence learning and memory performance, as demonstrated by their performance-improving action on rats in typical learning and memory models, such as water labyrinth, Morris labyrinth, passive avoidance and reminiscence tests in automated Skinner boxes. They have an antidepressant potential, as shown by their activity in the Porsolt rat swimming test.
Binding assays:

The binding affinities for PN 200-110 binding sites in the rat brain and rat heart were determined by the method of Rampe D. R., Mutledge A., Janis R. A., Triggle D. J.: Can. Journ. Physiol. Pharmacol. 65, (1987) 1452.
Water labyrinth:

Elderly Wistar rats (24 months) were placed at the start position in a plastic tank (120×50×40 cm) filled with cold (14°–15°) water and divided by vertical barriers. To arrive at a ladder which allows the animals to escape from the water, they must swim around these barriers. The time required to discover the exit and the number of errors on the route thereto are recorded. An error is defined as swimming into a dead end or swimming over the boundary line of imaginary squares, into which the tank is divided, in the direction away from the exit. The rats remain in the labyrinth until they find the exit, but for no longer than 300 seconds. They are then picked up, dried and warmed under a red lamp. Thereafter, they return to their home cages. In a typical experiment, two equivalent groups of animals (placebo, test substance, in each case n=15) are determined by a preliminary test. The animals then undergo 6 test sessions, two per day. The test substances or placebo are administered perorally 30 minutes before the experiments. A shortening of the time taken to reach the exit, a reduction in the number of errors and an increase in the number of animals which find the exit at all are a measure of the learning- and memory-improving action of the test substances in comparison with the placebo.
Porsolt rat swimming test During a preliminary test, young rats are placed in a glass cylinder (40 cm high, 20 cm diameter) filled to a height of 17 cm with water at 25° C. After 20 minutes in the water, the animals are taken out and warmed under a lamp for 30 minutes. In this preliminary test, all the rats attempt to escape from the cylinder until they remain immobile after about 15 minutes ("behavioral despair"). 24 hours later the test session starts, in which the rats are placed in the glass cylinder as on the previous day, but this time for only 5 minutes. The periods of time over which the rats remain immobile during these 5 minutes are recorded. A rat which performs only minimal movement to keep its head above water while holding itself vertical in the water is regarded as immobile. The placebo or test substances (0.25, 0.5, 1, 5, 10 mg/kg; n=6 in each group) are administered perorally three times: 23, 5 and 1 hour before the test session (1, 19, 23 hours after the preliminary test). The antidepressant action of the test substances is manifested in the reduction of the duration of immobility in comparison with the placebo values.

On the basis of their pharmacological properties, they can be employed for the preparation of medicaments for the treatment of centrally degenerative diseases, such as occur, for example, with dementias (multi-infarct dementia (MID), primary degenerative dementia (PDD), presenile and senile Alzheimer's disease, HIV dementia and other forms of dementia), Parkinson's disease or amyotropic lateral sclerosis.

The active compounds furthermore are suitable for the treatment of disturbances in cerebral performance in old age, organic brain syndrome (OBS) and age-associated memory impairment (AAMI).

They are useful for the prophylaxis of and for combating the consequences of disturbances in cerebral circulation, such as cerebral ischaemias, apoplexies and subarachnoid haemorrhages.

They are suitable for the treatment of depression and mania. Other fields of use are the treatment of migraine, of neuropathies which are caused, for example, by traumas, metabolic diseases, such as diabetes mellitus, intoxications, microorganisms or autoimmune diseases, and of addictions and withdrawal symptoms.

The compounds according to the invention are $Ca^{2+}$ antagonists having a selectivity for L-type $Ca^{2+}$ channels of the central nervous system.

This selectivity is superior to that of the known $Ca^{2+}$ antagonistic dihydropyridines nimodipine and nicardipine, which have a cerebral activity. This manifests itself, for example, by comparison of the binding affinities for DHP (PN-200 110) binding sites in the rat brain and rat heart [cf. Rampe, D. R., Rutledge, A., Janis, R. A., Triggle, D. J., Can. Journ. Physiol. Pharmacol. 65 (1987), 1452].

| Example No. | $K_i$ (Brain) [nM] | $K_i$ (Heart) [nM] | Selectivity |
|---|---|---|---|
| Nimodipine | 2.4 | 4.6 | 1.9 |
| Nicardipine | 32 | 14 | 0.44 |
| 21 | 13 | 78 | 6.0 |

The present invention also relates to pharmaceutical formulations which, in addition to inert, non-toxic, pharmaceutically suitable auxiliaries and excipients, comprise one or more compounds of the general formula (I) or which consist of one or more active compounds of the formula (I), and to processes for the preparation of these formulations.

The active compounds of the formula (I) should be present in these formulations in a concentration of from 0.1 to 99.5% by weight, preferably from 0.5 to 95% by weight of the total mixture.

In addition to the active compounds of the formula (I), the pharmaceutical formulations can also comprise other pharmaceutical active compounds.

The abovementioned pharmaceutical formulations can be prepared by known methods in a customary manner, for example with the auxiliary(ies) or excipient(s).

In general, it has proved advantageous to administer the active compound or compounds of the formula (I) in total amounts of from about 0.01 to about 100 mg/kg, preferably in total amounts of from about 0.1 mg/kg to 20 mg/kg of body weight every 24 hours, if appropriate in the form of several individual doses, to achieve the desired result.

However, if appropriate, it may be advantageous to deviate from the amounts mentioned, and in particular as a function of the nature and body weight of the subject to be treated, of the behaviour of the individual towards the medicament, of the nature and severity of the disease, of the nature of the formulation and administration and of the time or interval at which administration takes place.

Unless noted otherwise, the particular $R_f$ values stated were determined by thin layer chromatography on silica gel (aluminium foil, silica gel 60 F 254, E. Merck). The substance spots were visualized by observation under UV light and/or by spraying with 1% strength potassium permanganate solution or with molybdatophosphoric acid solution.

The flash chromatography was carried out on silica gel 60, 0.040–0.064 mm, E. Merck (see Still et al., J. Org. Chem. 43, 2923, 1978; for simpler separation problems, see Aldrichimica Acta 18, 25, 1985). Elution with solvent gradients means: starting with the pure, non-polar solvent mixture component, the polar mobile phase component is admixed to an increasing extent, until the desired product is eluted (monitoring by thin layer chromatography).

In the case of all the products, the solvent was distilled off under finally about 0.1 mm Hg.

STARTING COMPOUNDS

Example I

2-Methoxyethyl 2-acetyl-3-(2,4-difluorophenyl)-2-propenoate

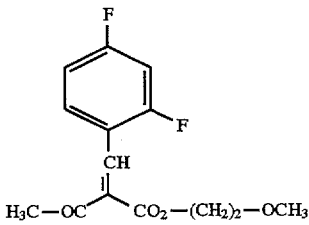

5.0 g (35mmol) of 2,4-difluorobenzaldehyde are dissolved with 5.7 g (35 mmol) of 2-methoxyethyl acetoacetate in 100 ml of isopropanol. A freshly prepared solution of 1.0 ml of piperidine and 0.5 ml of glacial acetic acid in 5 ml of isopropanol is added and the mixture is stirred at 40° C. overnight. The mixture is concentrated, the residue is taken up in toluene, this mixture is concentrated again and the residue is purified by filtration over 100 ml of silica gel (mobile phase: toluene/ethyl acetate 100:1) to give 5 g of the target compound as a yellow oil, which is immediately reacted further.

Example II 4-(2-Chloro-6-fluorophenyl) -1,4-dihydro-2,6-dimethylpyridine-3,5-dicarboxylic acid monocyclopentyl ester

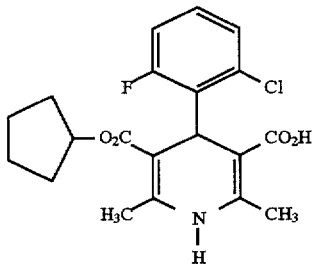

98 g (0.22 mol) of 2-cyanoethyl cyclopentyl 4-(2-chloro-6-fluorophenyl) -1,4-dihydro-2,6-dimethylpyridine-3,5-dicarboxylate are dissolved in 400 ml of 1,2-dimethoxyethane and the solution is stirred with 400 ml of 1N sodium hydroxide solution at room temperature overnight.

The solvent volume is reduced to about half, the concentrate is washed with methylene chloride and the aqueous phase is acidified with 2N hydrochloric acid (pH=2). Extraction twice with methylene chloride, washing of the organic phases with water, drying over sodium sulphate, concentration and crystallization from ether gives 42 g of the target compound as a solid of melting point about 120° C. (decomposition).

Example III

Cyclopentyl 4-(2-chloro-6-fluorophenyl)-1,4-dihydro-5-(1-imidazolylcarbonyl) -2,6-dimethylpyridine-3-carboxylate

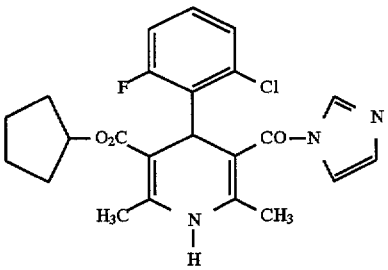

13.6 g (83 mmol) of carbonyldiimidazole are added to 33.0 g (83 mmol) of 4-(2-chloro-6-fluorophenyl) -1,4-dihydro-2,6-dimethylpyridine-3,5-dicarboxylic acid monocyclopentyl ester in 350 ml of tetrahydrofuran and the mixture is heated under reflux for 3 hours. Monitoring by thin layer chromatography (silica gel, toluene/ethyl acetate 1:1) shows complete conversion, after which the reaction mixture is concentrated, the residue is taken up in ethyl acetate and the mixture is washed twice with water, dried over sodium sulphate and concentrated again. The target compound precipitates from ether in the form of white crystals of melting point 150° C. Yield: 29.7 g

PREPARATION EXAMPLES

Example 1

2-Cyanoethyl cyclopentyl 4-(2-chloro-6-fluorophenyl) -1,4-dihydro-2,6-dimethylpyridine-3,5-dicarboxylate

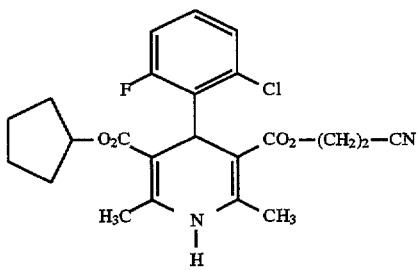

280 g (0.63 mol) of cyclopentyl 2-acetyl-3-(2-chloro-6-fluorophenyl) -2-propenoate are dissolved with 97.2 g (0.63 mol) of 2-cyanoethyl 3-amino-2-butenoate in 400 ml of isopropanol and the solution is heated under reflux for about 8 hours until monitoring by thin layer chromatography (silica gel, toluene/ethyl acetate 5:1) shows complete conversion. The reaction mixture is concentrated and the residue is taken up twice more with toluene and the mixture concentrated again. Filtration twice over 2 l of silica gel each time using a toluene/ethyl acetate gradient gives 160 g of the target compound as an oil. A portion is further purified by chromatography over silica gel and crystallization from ether to give a crystalline solid of melting point 135°–136° C.

Example 2

Cyclopentyl 2-fluoroethyl 4-(2-chloro-6-fluorophenyl)-1,4-dihydro-2,6-dimethylpyridine-3,5-dicarboxylate

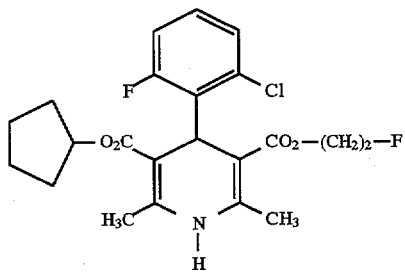

2.0 g of the compound from Example III are stirred in 20 ml of fluoroethanol at 100° C. for 12 hours and the excess alcohol is then distilled off. The crude product which remains is purified by filtration over silica gel in toluene and by chromatography over silica gel in methylene chloride/ethyl acetate 20:1. 0.9 g of the target compound is obtained in the form of a foam. Melting point: 55° C. $R_f$ (SiO$_2$, toluene/ethyl acetate 5/1) =0.30

The compounds listed in Tables 1, 2 and 3 are prepared analogously to the instructions of Examples 1 and 2:

TABLE 1

| Example No. | R$^4$ | Melting point [°C.]/R$_f$* | Preparation analogous to Example No. |
|---|---|---|---|
| 3 | cyclohexylmethyl | 100 | 2 |
| 4 | cyclohexylpropyl | 79–81 | 2 |
| 5 | cyclohexylbutyl | 66 | 2 |

TABLE 2

| Example No. | R$^1$ | R$^4$ | Melting point [°C.]/R$_f$* | Preparation analogous to Example No. |
|---|---|---|---|---|
| 6 | —CH(CH$_3$)$_2$ | —CH$_2$CH$_2$OCH$_2$CH$_2$OCH$_3$ | 128 | 2 |
| 7 | cyclopentyl | —CH$_2$CH$_2$CH$_2$OCH$_2$CH$_2$OCH$_3$ | 102 | 2 |

TABLE 3

[Structure: 1,4-dihydropyridine with 3-cyanophenyl at 4-position, R₁O-CO- and R₄O-CO- at 3,5-positions, methyl groups at 2,6-positions]

| Example No. | R¹ | R⁴ | Melting point [°C.]/$R_f$* | Preparation analogous to Example No. |
|---|---|---|---|---|
| 8 | —CH(CH₃)₂ | ~~~OCH₂CF₃ | 100 | 1 |
| 9 | —CH(CH₃)₂ | ~~~O-cyclohexyl | 107–108 | 2 |
| 10 | —C(CH₃)₃ | ~~~OCH₂CF₃ | 0.36 c) | 1 |
| 11 | cyclopentyl | ~~~OCH₂CF₃ | 116–117 | 1 |
| 12 | cyclopentyl | ~~~O-cyclohexyl | 92 | 2 |
| 13 | —(CH₂)₂—OCH₃ | ~~~cyclopentyl | 153–155 | 2 | c) = toluene:ethyl acetate 3:1

Example 14

Isopropyl 5-(3-phenylpropoxycarbonyl) -2,6-dimethyl-4-(2,3-dichlorophenyl) -1,4-dihydropyridine-3-carboxylate

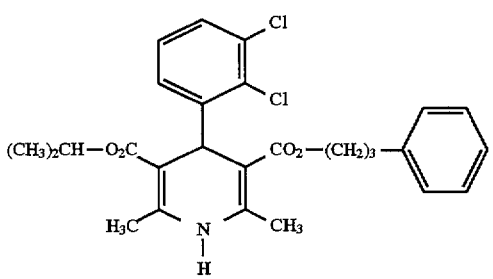

4.34 g (10 mmol) of 4-(2,3-dichlorophenyl) -1,4-dihydro-2,6-dimethylpyridine-3-isopropoxycarbonyl-3-carboxylic acid imidazolide, 1.63 g (12 mmol) of 3-phenylpropanol and 360 mg (12 mmol) of NaH (80% strength suspension) are stirred in 30 ml of absolute tetrahydrofuran at 40° C. for 1 hour (monitoring by thin layer chromatography). The solvent is distilled off in vacuo, the residue is taken up in 30 ml of ethyl acetate and the mixture is washed with 2N HCl solution and saturated NaCl solution. After drying over Na₂SO₄, the mixture is evaporated and the residue is purified by chromatography over silica gel (eluent: toluene/ethyl acetate 10:1). Yield: 43.1% $R_f$=0.36 (toluene/ethyl acetate 5:1)

Example 15

2-Methoxyethyl3-phenylpropyl4-(2,3-dichlorophenyl)-1,4-dihydro-2,6-dimethylpyridine-3,5-dicarboxylate

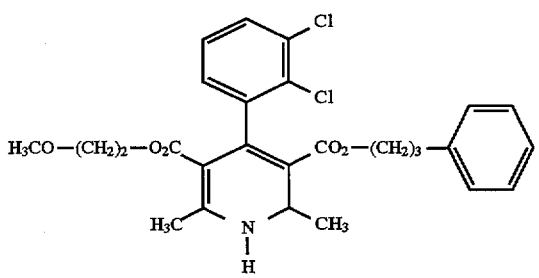

2.49 g (11.3 mmol) of 3-phenylpropyl acetoacetate and 1.81 g (11.3mmol) of 2-methoxyethyl β-aminocrotonate are added to a suspension of 2.00 g (11.3 mmol) of 2,3-dichlorobenzaldehyde in 23 ml of ethanol and the mixture is refluxed until the conversion is complete. For working up, the reaction mixture is taken up in 300 ml of ethyl acetate and the mixture is washed with water, sodium bicarbonate solution, water and saturated sodium chloride solution and dried over magnesium sulphate. After the solvent has been concentrated, the residue is chromatographed over silica gel (toluene/ethyl acetate 3:1) and the resulting crude product is crystallized from ethyl acetate/petroleum ether to give 1.47 g (26% of theory) of the target compound.

The compounds listed in Table 4 are prepared analogously to the instructions of Examples 1, 2, 14 and 15:

TABLE 4

[Structure: 1,4-dihydropyridine with phenyl substituted with $R_2$, $R_3$; ester groups $R_1O-CO-$ and $-CO-OR_4$; methyl groups at 2,6-positions; NH]

| Example No. | $R^1$ | $R^2$ | $R^3$ | $R^4$ | Melting point (°C.) | Preparation analogously to Example No. |
|---|---|---|---|---|---|---|
| 16 | $H_3CO-(CH_2)_2-$ | 2-CN | 3-Cl | cyclopropyl | 147–148 | 2 |
| 17 | $H_3CO-(CH_2)_2-$ | 2-CN | 3-Cl | 1-methylcyclopropyl | 122–123 | 2 |

| Example No. | $R^1$ | $R^2$ | $R^3$ | $R^4$ | Melting point (°C.) $R_f^*$ | Preparation analogously to Example No. |
|---|---|---|---|---|---|---|
| 18 | cyclopentyl | 2-F | 3-F | $-(H_2C)_2-$pyridyl | 145–146 | 14 |
| 19 | cyclopentyl | 2-F | 3-F | $-H_2C-$pyridyl | 121–122 | 14 |
| 20 | $-CH(CH_3)_2$ | 2-F | 3-F | $-H_2C-$(2-methoxyphenyl) | — | 14 |
| 21 | $-CH(CH_3)_2$ | 2-F | 3-F | $-H_2C-CH(OCH_3)(C_5H_6)$ (S) | 131 diastereomer mixture | 14 |
| 22 | $-CH(CH_3)_2$ | 2-F | 5-F | $-(CH_2)_2-F$ | 160 | 2 |
| 23 | cyclopentyl | 2-F | 5-F | $-(CH_2)_2-F$ | 147 | 2 |

| Example No. | $R^1$ | $R^2$ | $R^3$ | $R^4$ | Melting point (°C.) $R_f^*$ | Preparation analogously to Example No. |
|---|---|---|---|---|---|---|
| 24 | $-CH(CH_3)_2$ | 2-F | 3-F | $-H_2C-$pyridyl | 163 | 14 |

TABLE 4-continued

| 25 | —CH(CH₃)₂ | 2-F | 3-F | pyridin-2-yl-CH₂CH₂— | 111–112 | 14 |
| 26 | —CH(CH₃)₂ | 2-Cl | 3-CN | —(CH₂)₂—CN | 132–139 | 1 |

The compounds listed in Table 5 are prepared from the corresponding imidazolide analogously to the instructions of Example 14:

TABLE 5

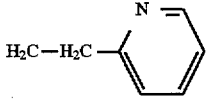

| Example No. | R¹ | R² | R³ | R⁴ | Melting point (°C.)/R_f* |
|---|---|---|---|---|---|
| 27 | cyclopentyl | 2-F | 3-F | —H₂C—(2-OCH₃-phenyl) | 114–116 |
| 28 | cyclopentyl | 2-F | 3-F | —H₂C—CH(OCH₃)(S)(phenyl) | 0.22ᵃ⁾ diastereomer mixture |
| 29 | —CH(CH₃)₂ | 2-F | 3-F | —H₂C—CH(OCH₃)(R)(phenyl) | 134–137 diastereomer mixture |
| 30 | —CH(CH₃)₂ | 2-F | 3-F | —H₂C—CH(OCH₃)(R)(phenyl) | 135–136 enantiomerically pure diastereomer |
| 31 | —CH₃ | 2-F | 3-F | pyridin-2-yl-(CH₂)₂— | 159–160 |
| 32 | —(CH₂)₂—OCH₃ | 2-F | 3-F | cyclopentyl-CH₂— | 83–84 |

TABLE 5-continued

[Structure: dihydropyridine core with R1-O2C, CO2-R4, H3C, CH3, NH, and aryl group with R2, R3 substituents]

| Example No. | R¹ | R² | R³ | R⁴ | Melting point (°C.)/R$_f$* |
|---|---|---|---|---|---|
| 33 | —(CH₂)₃—OCH₃ | 2-F | 3-F | cyclopentyl-CH₂— | 0.33[f] (oil) |
| 34 | cyclopentyl-CH₂— | 2-F | 3-F | —(CH₂)₂-pyridyl | 115–116 |
| 35 | —(CH₂)₂—OCH₃ | 2-F | 3-F | cyclohexyl-CH₂— | 87–88 |
| 36 | —(CH₂)₃—OCH₃ | 2-F | 3-F | cyclohexyl-CH₂— | 0.34[f] (oil) |
| 37 | cyclohexyl-CH₂— | 2-F | 3-F | —(CH₂)₂-pyridyl | 130–133 |
| 38 | —CH(CH₃)₂ | 2-Cl | H | —(CH₂)₂-pyridyl | 135–136 |

[a] = cyclohexane/ethyl acetate 7:3
[f] = cyclohexane/ethyl acetate = 1:1

We claim:

1. The compound which has the formula

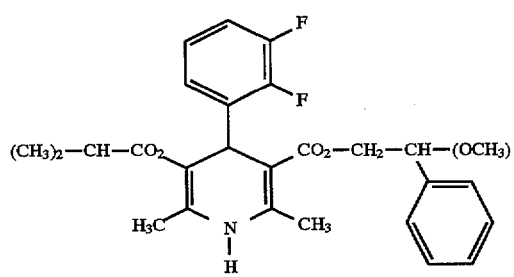

2. A pharmaceutical composition which comprises an effective amount of the compound according to claim 1 and a pharmaceutically acceptable auxiliary or additive.

3. A method of treating depression which comprises administering an effective amount of the compound according to claim 1 to a host in need thereof.

* * * * *